United States Patent [19]
Ishii et al.

[11] Patent Number: 5,360,737
[45] Date of Patent: Nov. 1, 1994

[54] *ENTEROBACTER CLOACAE* FERM BP1529 HAVING PLANT GROWTH ACCELERATORY ACTIVITY

[75] Inventors: Takafumi Ishii; Takashi Adachi; Toshio Yasumura; Shinji Miyadoh; Hidemasa Hidaka, all of Kanagawa, Japan

[73] Assignee: Meiji Seika Kaisha, Ltd., Tokyo, Japan

[21] Appl. No.: 115,667

[22] Filed: Sep. 2, 1993

Related U.S. Application Data

[63] Continuation of Ser. No. 754,255, Aug. 27, 1987, abandoned, which is a continuation of Ser. No. 109,649, Oct. 19, 1987, abandoned.

[30] Foreign Application Priority Data

Oct. 17, 1986 [JP] Japan .................................. 61-245399

[51] Int. Cl.$^5$ .......................... C12M 1/20; A01C 1/06; A01N 63/00
[52] U.S. Cl. .................................. 435/252.1; 435/828; 47/57.6; 424/93.48; 504/117
[58] Field of Search .......................... 47/57.6, 57.605; 435/252.31, 252.5, 252.1; 471/6, 65; 424/93 P; 504/117

[56] References Cited

FOREIGN PATENT DOCUMENTS

WO8700194 1/1987 WIPO .

OTHER PUBLICATIONS

Lasik et al (1979) Folia Microbio 24, pp. 262–265.
Grant et al. (1969) J. Bactereology pp. 1187–1193.
Lynch et al. (1984) *Proc. Inter. Symp. EEC Programmed Recycling of Urban and Industrial Waste.* Luxembourg, pp. 221–226.
Burgos-Leon. "A Case Study in Soil Fatigue Induced by Sagliocultivator" pp. 1–35.
Agronomie Tropicale, vol. 35, No. 4, 1980, pp. 319–334 no translation.
Plant and Soil, vol. 103, 1987, pp. 221–226.

*Primary Examiner*—Gary Benzion
*Attorney, Agent, or Firm*—Sughrue, Mion, Zinn, Macpeak & Seas

[57] ABSTRACT

A microorganism belonging to the genus Enterobacter and having a plant growth acceleratory activity, particularly *Enterobacter cloacae,* and a method for cultivating crops using the microorganism or polysaccharides produced therefrom are disclosed.

1 Claim, No Drawings

ENTEROBACTER CLOACAE FERM BP1529 HAVING PLANT GROWTH ACCELERATORY ACTIVITY

This is a continuation of application No. 07/754,255 filed Aug. 27, 1987, now abandoned which is a continuation of application No. 07/109,649 filed Oct. 19, 1987, now abandoned.

FIELD OF THE INVENTION

This invention relates to a novel microorganism having a plant growth acceleratory effect and a method for cultivating crops using the same.

BACKGROUND OF THE INVENTION

A wide variety of microorganisms live in the rooting zone (rhizosphere) or root surface of plants, giving great influences on growth of living organisms, outbreak of diseases of living organisms, and the like.

Attempts to separate industrially useful microorganisms and to utilize them for improvements of agricultural productivity have hitherto been made, and there are a number of reports of these studies.

For example, nitrogen-fixing bacteria fix nitrogen in the air to thereby provide plants with nitrogen, one of the three nutrients for plants. It is known that mycorrhiza enhance bioavailability of phosphorus in the soil and accelerate the growth of plants by providing them with phosphorus, an essential element for plants. Further, while a variety of pathogenic bacteria causative of plant diseases inhabit the soil, it is known that microorganisms antagonizing these pathogenic bacteria also exist in the soil. For example, bacteria belonging to the genus Pseudomonas have been isolated as antagonistic microorganisms and studied for their utility.

However, since culture of mycohhriza requires plant bodies because of their symbiotic relationship with plant roots, it has been difficult to mass-culture them on an industrial scale. Practical utilization of mycohhrize, therefore, has not yet been established. Although the nitrogen-fixing bacteria can be industrially mass-cultured, when they are scattered in the soil, the number of microbial cells decreases with time, resulting in reduction of a level of the fixed nitrogen. This gives rise to an economical problem when compared with the use of commercially available nitrogeneous fertilizers. In addition, many of the above-described antagonistic bacteria produce antagonists against growth of pathogenic bacteria, i.e., antibiotics, which sometimes have more or less inhibitory effects on plant growth.

SUMMARY OF THE INVENTION

One object of this invention is to provide a useful microorganism isolated from the rhizosphere of plants, which can easily be cultured on an industrial scale, exhibits satisfactory fixation to the rhizosphere or root surface of plants, and produces a plant growth acceleratory activity.

Another object of this invention is to provide a method of utilizing such a microorganism for improving efficiency of crop production.

In order to accomplish the above objects, the inventors have screened microorganisms capable of accelerating plant growth from the rhizosphere of plants. As a result, it has now been found that a novel microorganism belonging to the genus Enterobacter isolated from the soil in the rhizosphere of cucumber, i.e., *Enterobacter cloacae*, serves the purposes of the present invention, such as acceleration of growth of various kinds of agriculturally useful plants including cucumber. The present invention has been completed based on this finding.

The present invention provides *Enterobacter cloacae* having a plant growth acceleratory activity.

The present invention further provides a method for cultivating crops which comprises applying directly onto seeds a microorganism belonging to the genus Enterobacter and having a plant growth acceleratory activity, and the like and sowing the soil with the thus treated seeds, or mixing the microorganism with the soil and sowing the thus treated soil with seeds.

The present invention furthermore provides a method for cultivating crops by hydroponics which comprises using a liquid fertilizer containing a microorganism belonging to the genus Enterobacter and having a plant growth acceleratory activity.

The present invention still further provides a method of cultivating crops which comprises applying directly onto seeds a polysaccharide produced by a microorganism belonging to the genus Enterobacter and having a plant growth acceleratory activity, and sowing the soil with the treated seeds, or mixing the polysaccharide with the soil and sowing the treated soil with seeds, or spraying the polysaccharide onto foliage of crops.

DETAILED DESCRIPTION OF THE INVENTION

The microorganism belonging to the genus Enterobacter and having a plant growth acceleratory activity, *Enterobacter cloacae*, according to the present invention can be isolated from the soil in the rhizosphere of cucumber and has the following microbiological properties.

1. Morphological Properties
   (1) Shape and Size: bacillus, 0.8 to $1.0 \times 1.5$ to 3.0 $\mu$m
   (2) Polymorphism: none
   (3) Motility: mobile with peritrichous flagella
   (4) Spore: none
   (5) Gram's Stain: negative
   (6) Acid-Fast Staining: negative
2. Growth in Various Media
   (1) Meat Extract-Agar Plate Culture: Microbial cells do not produce any distinguished pigments but vigorously grow to assume a pale yellow cream.
   (2) Meat Extract-Agar Slant Culture: The same as (1) above.
   (3) Meat Extract Liquid Culture: The whole fungus body grows with becoming turbid. No pellicle is formed.
   (4) Meat Extract-Gelatin Stab Culture: Extremely slow liquefaction occurs.
   (5) Milk Culture: No marked changes in liquefaction, coagulation, pH change, etc., are noted.
3. Physiological Properties
   (1) Reduction of Nitrate: positive
   (2) Denitrification Reaction: negative
   (3) MR Test: negative
   (4) VP Test: positive
   (5) Indole Formation: negative
   (6) Hydrogen Sulfide Formation: negative
   (7) Starch Hydrolysis: negative
   (8) Utilization of Citric Acid: positive
   (9) Inorganic Nitrogen Source: Nitrates and ammonium salts are utilized as a nitrogen source.
   (10) Pigment Formation: No noticeable production of soluble or insoluble pigments is observed.

(11) Urease: positive
(12) Oxidase: negative
(13) Catalase: positive
(14) Growth Range: Growth temperature ranges from 15° to 45° C., with optimal temperature ranging from 28° to 37° C. and suitable growth pH is in the vicinity of neutrality.
(15) Behavior to Oxygen: facultative anaerobic
(16) O-F Test: F type
(17) Acid and Gas Formation from Saccharides;

| Saccharide | Acid Formation | Gas Formation |
|---|---|---|
| L-arabinose | + | − |
| D-xylose | + | + |
| D-glucose | + | + |
| D-mannose | + | + |
| D-fructose | + | + |
| D-galactose | + | + |
| maltose | + | + |
| sucrose | + | + |
| lactose | + | + |
| trehalose | + | + |
| D-sorbitol | + | + |
| D-mannitol | + | + |
| inocitol | + | − |
| glycerin | − | − |
| starch | − | − |
| adonitol | − | − |

4. Other Properties
(1) Production of DNase: negative
(2) Production of Tryptophane Deaminase: negative
(3) Production of β-Galactosidase: positive
(4) Arginine Decomposition Test: positive
(5) Lysine Decarboxylation Reaction: negative
(6) Ornithine Decarboxylation Reaction: positive
(7) Aesculin Decomposition: negative As shown above, the strain of the invention has morphological properties such that it is a Gram-negative and facultatively anaerobic bacillus which does not form spores and moves by peritrichous flagella; and physiological properties such that it is negative to oxidase and positive in nitrate reduction. From these properties, this strain is judged to belong to the family Enterobacteriaceae. Further, in view of other various physiological properties, it is most reasonable to consider that the strain belongs to *Enterobacter cloacae*. The strain has been deposited to the Agency of Fermentation Research Institute, Japan as BIKOKEN-KIN KI No. 8968 (FERM BP-1529).

According to the cultivation method of the present invention, in order to accelerate growth of plants the above-described microorganism belonging to the genus Enterobacter and having a plant growth acceleratory activity, e.g., *Enterobacter cloacae*, can be applied onto seeds in an amount of from $10^6$ to $10^{10}$ cells per seed and directly sowing the soil with the thus treated seeds. Alternatively, the microorganism can be mixed with the soil in an amount of from $10^5$ to $10^{10}$ cells per gram of soil and sowing the thus treated soil with seeds.

In the case of hydroponics, the above-described microorganism can be mixed with a liquid fertilizer for hydroponics in an amount of from $10^6$ to $10^8$ cells/ml and, if desired, the microorganism may be additionally supplied during cultivation.

The inoculation of the microorganism of the present invention shows its effects first in acceleration growth of a root system and then in acceleration growth of a leaf and stem part.

As described above, the microorganisms belonging to the genus *Enterobacter*, and particularly *Enterobacter cloacae*, are capable of accelerating plant growth when applied onto seeds, etc., or mixed with the soil. It has further been found that extracellular polysaccharides produced by cultivation of *Enterobacter cloacae* show the similar plant growth acceleratory effect.

The aforesaid polysaccharides can be produced by cultivating *Enterobacter cloacae* (FERM BP-1529) in an M-agar medium comprising the same composition as M medium as used in Example 1 about to be described plus 0.0033 wt % Rose Bengal and 1.5 wt % agar, at 30° C. on an experimental base. On an industrial scale, the polysaccharides can be produced by shake culture of *Enterobacter cloacae* (FERM BP-1529) in a liquid medium containing, for example, 1 wt % lactose, 0.5 wt % peptone, 0.1 wt % $KH_2PO_4$, and 0.05 wt % $MgSO_4.7H_2O$, at 30° C. for 2 to 3 days, subjecting the resulting culture to centrifugal separation to remove the fungus body, concentrating the supernatant liquor to one-third of its original volume, adding to the concentrate three times as much volume ethanol to precipitate the produced polysaccharides, and isolating and drying them to obtain from 0.6 to 1.2 g of polysaccharides per liter of the culture.

The thus obtained polysaccharides are water-soluble. The polysaccharides, when applied to plants, accelerate growth of the root and shoot systems of the plants, resulting in increased yields. In carrying out their application to plants, the polysaccharides may be directly coated onto seeds in an amount of from 5 to 100 γ/seed; or a 50 to 200 γ/ml aqueous solution of the polysaccharides may be sprayed over the soil in an amount of from 0.5 to 5.0 Kg/ha; or a 20 to 200 γ/ml aqueous solution of the polysaccharides may be sprayed on the foliage according to foliar spray treatment. Further, the polysaccharides may be incorporated into a liquid fertilizer for hydroponics. By these treatments, the yields of crops can be increased, and the thus cultivated crops have excellent taste and quality, as expressed, for example, by improved starch content.

The plants to which the present invention is applicable are not particularly limited and preferred ones are crops. The term "crops" as used herein means all kinds of agricultural plants and harvests therefrom, such as grains, vegetables, flowers, fruit trees, and the like. The plants also include seedlings of vegetables, e.g., cucumbers, pumpkins, egg plants, tomatoes, melons, water melons, etc.; seedlings of flowers, seedlings of grains, and seedlings of all other useful plants. The term "seeds, etc." as used herein means not only seeds but seed potatoes for tuberous root, etc. The term "hydroponics" as used herein includes water culture, sand culture, gravel culture, rock wool culture, and the like.

The present invention will now be described in detail with reference to the following examples, but it should be understood that the present invention is not limited thereto. In these examples, all the percents are by weight unless otherwise indicated.

EXAMPLE 1

(1) Mass Culture of *Enterobacter cloacae*

In a 1-l three-necked flask was placed 400 ml of a liquid culture medium containing 1.0% glucose, 0.5% peptone, 0.1% $KH_2PO_4$, and 0.05% $MgSO_4.7H_2O$ (hereinafter referred to as M medium). After sterilizing at 120° C. for 30 minutes, the medium was cooled and a platinum loopful of *Enterobacter cloacae* (FERM BP-1529) was inoculated to the medium and cultured at 240 rpm for 24 hours at 30° C. to prepare a seed culture. A 30-l jar fermentor was charged with 20 l of M medium, and the medium was sterilized at 120° C. for 30 minutes. After cooling to 30° C., the medium was inoculated with the above-obtained seed culture and cultured at 200 rpm for 24 hours at 30° C. under aeration of 100 vvm. The resulting culture contained $1 \times 10^{10}$ cells/ml *Enterobacter cloacae*.

(2) Nursing of Cucumber

Soil for nursery was put in a nursery tray (30 cm × 50 cm × 3 cm), and 100 seeds of cucumber (variety: Kifujin) were sown thereon. After cultivation at 20° to 23° C. for one week, the cucumber seedlings were planted in a pot (diameter 90 mm; height 76 mm) and further nursed for 2 weeks. The experiment groups used were as follows.

Control Group: The nursery was used as it was.
Soil Treatment Group: *Enterobacter cloacae* ($10^7$ cells/g-soil) was added to the nursery soil.
Seed Treatment Group: The seeds (Kifujin) were dipped in the culture of *Enterobacter cloacae* ($1.0 \times 10^{10}$ cells/ml) and then nursed in the soil free of *Enterobacter cloacae*.

The results are shown in Table 1 below. Table 1 indicates that the proportion of seedlings of S size having an above ground height of 10 cm or less was 37% in Control Group, while those in Soil Treatment Group and Seed Treatment Group were smaller than that in Control Group, as being 6% and 18%, respectively. Thus, it has been proved that larger and stronger seedlings can be obtained when either soil or seeds are treated with *Enterobacter cloacae*.

TABLE 1

| Size of Seedling* | Control Group | Soil Treatment Group | Seed Treatment Group |
|---|---|---|---|
| L | 13% | 39% | 30% |
| M | 50% | 55% | 52% |
| S | 37% | 6% | 18% |

Note:
*Size L: above ground height 15 cm or more
Size M: above ground height from 10 to 15 cm
Size S: above ground height 10 cm or less (3) Culture of Cucumber The cucumber seedlings as obtained in (2) above were planted in the soil in a greenhouse at intervals of 80 cm and cultivated in a greenhouse under conditions of natural temperature and natural light for 3 months. An inorganic fertilizer (Kasei No. 14: 14% $NH_4$-N, 10% P, 13% K) was applied to the base when needed. Further, in order to combat aphids, "Daisiston" (a preparation of 5% O,O-diethyl-S-2-(ethylthio)ethylphosphorodithioate) was sprayed, if desired, after the end of the 2nd week of culture. The results are shown in Table 2.

Table 2 indicates that the cucumber plants of both Soil Treatment Group and Seed Treatment Group had longer above ground heights than those of Control Group and the yield of cucumbers was 8 to 12% higher than that of Control Group.

TABLE 2

| Group | Above ground Average Height* (cm) | Yield (Kg/plant)* |
|---|---|---|
| Solid Treatment Group | 432 (120)** | 5.49 (112)** |
| Seed Treatment Group | 428 (119) | 5.30 (108) |
| Control Group | 360 (100) | 4.91 (100) |

Note:
*n = 16
**Values in the parentheses are relative values taking the result of Control Group as a standard (100) (the same applies hereinbelow).

(4) Fixation of *Enterobacter cloacae* to Root Surface

The roots of the cucumber plants were sampled with a certain time interval during the culture, and the number of cells of *Enterobacter cloacae* grown on the roots was counted. the cell counting was carried out according to the method described in Dojo Biseibutsu Kenkyukai (ed.), *Dojo Biseibutsu Jikkenho* (Procedures of Experiments of Soil Microorganisms, Yokendo, Tokyo, Japan (1975)), p. 380. Since *Enterobacter cloacae* assumes a characteristic tone and shape and produces polysaccharides when cultured in a Martin medium (glucose=1%; peptone=0.5%, $KH_2PO_4$=0.1%; $MgSO_4.7H_2O$=0.05%; Rose Bengal=0.0033%; agar=2.0%; pH=6.8) at 30° C. for 24 to 48 hours, the number of colonies were counted using these properties as indications. The results are shown in Table 3. In Table 3, the number of cells was expressed in terms of the number of viable cells per g of the root (wet weight).

TABLE 3

| Group | 2 Weeks | 5 Weeks | 15 Weeks |
|---|---|---|---|
| Control Group | $1.2 \times 10^4$ | $4.2 \times 10^4$ | $3.8 \times 10^4$ |
| Seed Treatment Group | $4.1 \times 10^6$ | $1.1 \times 10^7$ | $1.8 \times 10^7$ |
| Soil Treatment Group | $4.0 \times 10^6$ | $2.0 \times 10^7$ | $3.2 \times 10^7$ |

EXAMPLE 2

Two sunny lettuce seeds were placed on a 4 cm-square urethane mat and immersed in a liquid fertilizer containing 0.15% of Otsuka House Hiryo No. 1 (10% N, 8% $P_2O_5$, 24% $K_2O$, 5% MgO, 0.1% MnO, 0.1% $B_2O_3$, 0.18% Fe), and 0.1% of Otsuka House Hiryo No. 2 (11% N, 23% CaO). After nursing for 10 days under conditions of 24° C. and 5,000 lux, the seedlings were planted in an apparatus for hydroponics and cultured for 35 days under conditions of 24° C. and 8,000 lux. The experiment groups used were as follows.

Control Group: Otsuka House Fertilizer group free of microorganism.
Treatment Group: *Enterobacter cloacae* was added to Otsuka House Fertilizer in a ratio of from $1 \times 10^5$ cells/ml to $1 \times 10^9$ cells/ml. During the culture, *Enterobacter cloacae* was added once a week (4 times in all). The strain added had been obtained in the same manner as in Example 1.

The results are shown in Table 4 below.

TABLE 4

| Group | Number of Cells Added (cells/ml) | Average Weight of Harvest/Plant (g) | Average Weight of Root (g) |
|---|---|---|---|
| Treatment Group | $1 \times 10^5$ | 39 | 7.9 |
| | $1 \times 10^6$ | 54 | 10.6 |

TABLE 4-continued

| Group | Number of Cells Added (cells/ml) | Average Weight of Harvest/Plant (g) | Average Weight of Root (g) |
| --- | --- | --- | --- |
|  | $1 \times 10^7$ | 73 | 11.1 |
|  | $1 \times 10^8$ | 70 | 12.3 |
|  | $1 \times 10^9$ | 40 | 8.4 |
| Control Group | 0 | 38 | 7.6 |

Note: n = 16

It can be seen from Table 4 that the harvest and root weight can be increased by the addition of *Enterobacter cloacae* to the liquid fertilizer. This effect was particularly remarkable in the groups where $1 \times 10^6$ to $1 \times 10^8$ cells/ml strain were added.

EXAMPLE 3

On black soil in a nursery box (50 cm × 15 cm × 20 cm) was dispersed 40 g of rice seeds (variety: Akinishiki), and the seeds were covered with the soil to a thickness of 3 to 4 mm. The seeds were cultured at 30° to 32° C. for 2 days for germination and then at 25° C. for 17 days. the experiment groups used were as follows.

Control Group: Untreated soil (black soil) was used.
Treatment Group: The soil was treated by addition of $1.0 \times 10^7$ cells/g *Enterobacter cloacae*. The strain used had been obtained in the same manner as in Example 1.

As a result, the average length of cormus of Treatment Group was 18.4 cm, showing an increase of 13% as compared with that of Control Group being 16.3 cm.

EXAMPLE 4

In a pot (50 cm × 15 cm × 20 cm) were planted 200 spinach seeds (variety: Jiromaru), and cultured for 40 days under conditions of 20° C. and 30,000 lux. The experiment groups used were as follows.
Control Group: Untreated soil (black soil) was used.
Treatment Group: The soil was treated by adding $1.0 \times 10^8$ cells/g *Enterobacter cloacae*. The strain had been obtained in the same manner as in Example 1. The results are shown in Table 5.

TABLE 5

| Group | Average Height (cm) | Average Weight (g) |
| --- | --- | --- |
| Treatment Group | 20.1 | 15.7 |
| Control Group | 17.5 | 11.8 |

As is apparent from Table 5, the average weight of the harvest from Treatment Group was 135% of that of Control Group.

EXAMPLE 5

One corn seed was sown in black soil in a pot (diameter 90 mm; height 76 mm) and cultured for 20 days under conditions of 25° C. and 5,000 lux. The experiment groups used were as follows.
Control Group: Untreated black soil was used.
Treatment Group: The soil was treated by adding $1 \times 10^4$ to $1 \times 10^9$ cells/g *Enterobacter cloacae*. The strain had been obtained in the same manner as in Example 1.
The results are shown in Table 6.

TABLE 6

| Group | Number of Cells Added (cells/g-Soil) | Average Length of Leaf and Stem (cm) |
| --- | --- | --- |
| Treatment Group | $1 \times 10^4$ | 37.8 |
|  | $1 \times 10^5$ | 42.3 |
|  | $1 \times 10^6$ | 44.5 |
|  | $1 \times 10^7$ | 51.5 |
|  | $1 \times 10^8$ | 48.4 |
|  | $1 \times 10^9$ | 36.4 |
| Control Group | 0 | 37.2 |

Note: n = 6

It can be seen from Table 6 that the addition of *Enterobacter cloacae* to the soil is effective to increase the leaf and stem length of the plant. In particular, the groups in which the soil was treatd with $1 \times 10^5$ to $1 \times 10^8$ cells/g of the strain exhibited growth acceleration of from 14 to 37% over Control Group.

EXAMPLE 6

Fourty grams of rice seeds (variety: Akinishiki) were dispersed on black soil in a nursery box (50 cm × 15 cm × 20 cm), and covered with the soil to a thickness of 3 to 4 mm. After culturing at 30° to 32° C. for 7 days, the roots of young seelings were dipped in a suspension containing $1 \times 10^5$/ml to $1 \times 10^{10}$/ml viable cells of *Enterobacter cloacae*, and the culturing was further continued for 10 days. In this example, fertilization and watering were carried out in the conventional manner. The viable cells of the strain used had been prepared in the same manner as in Example 1. The results are shown in Table 7.

TABLE 7

| Group | Number of Cells in Suspension (cells/ml) | Average Length of Leaf and Stem (cm) |
| --- | --- | --- |
| Treatment Group | $1 \times 10^5$ | 18.0 (103) |
|  | $1 \times 10^6$ | 18.4 (106) |
|  | $1 \times 10^7$ | 18.7 (107) |
|  | $1 \times 10^8$ | 19.0 (109) |
|  | $1 \times 10^9$ | 18.9 (109) |
|  | $1 \times 10^{10}$ | 19.2 (110) |
| Control Group | 0 | 17.4 (100) |

Note: n = 15

As is apparent from Table 7, growth of seedlings can be accelerated by inoculating *Enterobacter cloacae* to the roots of seedlings.

EXAMPLE 7

Fifty-six potato seeds (variety: Danshaku) were planted in an experimental field of 10.8 m² per group on February 27 and cultured up to May 29. During the culturing, fertilization and watering were carried out in the conventional manner. The experiment groups used were as follows.
Soil Treatment Group: The soil was treated by adding $1 \times 10^7$ cells/g *Enterobacter cloacae*.
Seed Treatment Group: The potato seeds were treated by coating each seed with $1 \times 10^{10}$ cells of *Enterobacter cloacae*.
Control Group: No treatment was effected to either soil or potato seeds.

The *Enterobacter cloacae* used was viable cells obtained in the same manner as in Example 1. The results are shown in Table 8 below.

TABLE 8

| Group | Yield of Potato (g/plant) | Starch Content (%) |
|---|---|---|
| Soil Treatment Group | 526.4 (113) | 9.25 (108) |
| Seed Treatment Group | 510.3 (100) | 9.54 (112) |
| Control Group | 464.3 (100) | 8.54 (100) |

Table 8 shows that the harvest yield and starch content increase to 110 to 113% and 108 to 112%, respectively, by treating the soil or seed potatoes with *Enterobacter cloacae* in an amount of $1 \times 10^7$ cells/g or $1 \times 10^{10}$ cells/seed potato, respectively, as compared with Control Group.

EXAMPLE 8

One part by weight of seeds of Kaiware Daikon (literally, cotyledon radish, artificially-grown radish having white stalk and cotyledon) were sprayed with an aqueous solution containing from 0.7 to 0.025% polysaccharides produced by *Enterobacter cloacae* (FERM BP-1529) and 0.75% sodium alginate, and dried in an air stream of 40° to 50° C. to prepare seeds coated with different amounts from 2.5 to 100 γ of the polysaccharides.

Fifty of the thus obtained polysaccharide-coated seeds were scattered on a synthetic resin-made mat placed in a glass container, and 70 ml of tap water was added thereto. The seeds were cultured at 23° C. in the dark for 4 days and then for 2 days under lighting of 5,000 lux. As a control group, untreated seeds were similarly cultured. The results are shown in Table 9.

TABLE 9

| Coated Amount of Polysaccharide (γ/seed) | Average Length of Leaf and Stem (cm) | Average Length of Root (cm) |
|---|---|---|
| 100 | 7.97 (120) | 11.4 (218) |
| 50 | 7.50 9113) | 10.2 (196) |
| 25 | 7.30 (110) | 8.60 (165) |
| 5 | 7.17 (108) | 6.30 (121) |
| 2.5 | 6.65 (100) | 5.31 (102) |
| Control | 6.64 (100) | 5.21 (100) |

Note: n = 25

As is clear from the results of Table 9, treatment of seeds with from 5 to 100 γ/seed polysaccharides produced by *Enterobacter cloacae* is effective to accelerate the growth to 108 to 120% in leaf and stem height and 121 to 218% in root length as compared with Control Group in which untreated seeds were used.

The extracellular polysaccharides used in this example had been prepared from *Enterobacter cloacae* as follows.

In a 250-ml three-necked flask was placed 30 ml of a medium containing 1% lactose, 0.5% peptone, 0.1% $KH_2PO_4$, and 0.05% $MgSO_4.7H_2O$. The medium was sterilized at 120° C. for 15 minutes, and it was then inoculated with a platinum loopful of *Enterobacter cloacae* (FERM BP-1529) and cultured at 240 rpm for 24 hours at 30° C. to prepare a first seed culture. In a 1-l three-necked flask was placed 300 ml of the above medium. After sterilization at 120° C. for 15 minutes, 10 ml of the above prepared seed culture was inoculated thereto, followed by cultivation at 240 rpm for 24 hours at 30° C. to obtain a second seed culture.

In a 30-l jar fermentor was placed 20 l of a medium having the same composition as the above medium and sterilized at 120° C. for 30 minutes. To the medium was inoculated 100 ml of the second seed culture which was cultured at 30° C. and 240 rpm for 2 days. To the culture was added an equal volume of water, and the culture was centrifuged at 10,000G for 40 minutes to remove the fungus body. The supernatant liquor was concentrated to a volume of 3 l, and 7 l of ethanol was added to the concentrate to precipitate the polysaccharides produced. The precipitate was collected by centrifugation and dried to yield 16 g of the polysaccharides.

EXAMPLE 9

The polysaccharides produced by *Enterobacter cloacae* in the same manner as in Example 8 were used for studying their plant growth acceleratory activity to Kaiware radish as follows.

Thirty-six seeds of kaiware Daikon were scattered on a synthetic resin mat put in a glass container, and 70 ml of tap water containing the polysaccharides in concentrations of from 0.000025 to 0.25% was added to the container, followed by culturing at 23° C. for 4 days in the dark and then for 2 days under lighting of 5,000 lux. The results are shown in Table 10.

TABLE 10

| Conc. of Polysaccharides (%) | Leaf and Stem Length Index* (%) | Root Length Index* (%) |
|---|---|---|
| 0.25 | 118 | 212 |
| 0.025 | 120 | 201 |
| 0.0025 | 116 | 165 |
| 0.00025 | 106 | 121 |
| 0.000025 | 98 | 101 |

Note: *n = 36

The average indices obtained under the same conditions as described above except for using tap water free of polysaccharides, was taken as a standard (100).

Table 10 indicates that in hydroponics the use of water containing from 0.25 to 0.00025% of the polysaccharides produced by *Enterobacter cloacae* accelerates the growth of both the leaf and stem part and the root part.

EXAMPLE 10

Fifty-six potato seeds (variety: Danshaku) were planted in an experimental field (10.8 m2/group) on February 27 and cultured for 2 months. The extracellular polysaccharides produced by *Enterobacter cloacae* in the same manner as in Example 8 were diluted with water to concentrations shown below and sprayed twice onto the leaf surface in the budding phase (on April 28 and May 8). The culture was completed on May 29. The test results are shown in Table 11 below.

TABLE 11

| Group No. | Conc. of Polysaccharide (γ/ml) | Yield of Potato (g/plant) | Starch Content (%) |
|---|---|---|---|
| 1 | 200 | 510.7 (110) | 9.96 (117) |
| 2 | 20 | 482.9 (104) | 9.32 (109) |
| 3 | 2.0 | 455.0 (98) | 8.65 (101) |
| 4 (Control) | 0 | 464.3 (100) | 8.54 (100) |

As can be seen from Table 11, the foliage-spraying treatment with 200 γ/ml to 20 γ/ml of the polysaccharides produced by *Enterobacter cloacae* increases the yield and the starch content.

EXAMPLE 11

In a pot (17 cm × 60 cm × 15 cm) was placed 9 Kg of black soil, and 40 seeds of Chinese cabbage (Brassica Rapa var. pervidis.) (variety: Misugi) were planted therein and cultured under natural conditions from June 15 to July 4. During the culture, the pot was watered with the aqueous solutions of the polysaccharides produced by *Enterobacter cloacae* in the same manner as in Example 8, having the concentrations shown in Table 12 below. the results are shown in Table 12.

TABLE 12

| Group No. | Conc. of Polysaccharide (γ/ml) | Watering Rate (Kg/ha) | Average Weight per Plant (g) |
|---|---|---|---|
| 1 | 200 | 5 | 5.76 ± 2.4 (120) |
| 2 | 100 | 2.5 | 5.38 ± 1.8 (112) |
| 3 | 50 | 0.5 | 5.33 ± 1.6 (111) |
| 4 | 0 | — | 4.80 ± 1.6 (100) |
| (Control) | | | |

Note: n = 40

Table 12 shows that the watering with 0.5 Kg/ha to 2.5 Kg/ha of the polysaccharides produced by *Enterobacter cloacae* increases the yield to 111 to 120%.

As described above, the present invention provides a novel microorganism having a plant growth acceleratory effect, and the use of this microorganism improves efficiency in crop cultivation.

While the invention has been described in detail with reference to specific embodiments thereof, it will be apparent to one skilled in the art that various changes and modifications can be made therein without departing from the spirit and scope of the invention.

What is claimed is:

1. A biologically pure culture of *Enterobacter cloacae* having plant growth acceleratory activity and having deposit number FERM BP 1529.

* * * * *